(12) United States Patent
Song et al.

(10) Patent No.: US 7,425,629 B2
(45) Date of Patent: Sep. 16, 2008

(54) STEREOSELECTIVE SYNTHESIS OF CERTAIN TRIFLUOROMETHYL-SUBSTITUTED ALCOHOLS

(75) Inventors: Jinhua J. Song, Hopewell Junction, NY (US); Jonathan T. Reeves, New Milford, CT (US); Frank Roschangar, Glen Allen, VA (US); Zhulin Tan, Danbury, CT (US); Nathan K. Yee, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 242 days.

(21) Appl. No.: 11/537,762

(22) Filed: Oct. 2, 2006

(65) Prior Publication Data

US 2007/0100142 A1 May 3, 2007

Related U.S. Application Data

(60) Provisional application No. 60/722,145, filed on Sep. 30, 2005.

(51) Int. Cl.
| | |
|---|---|
| *C07D 471/02* | (2006.01) |
| *C07D 491/02* | (2006.01) |
| *C07D 498/02* | (2006.01) |
| *C07D 513/02* | (2006.01) |
| *C07D 515/02* | (2006.01) |
| *C07D 257/08* | (2006.01) |
| *C07D 257/12* | (2006.01) |
| *C07D 251/00* | (2006.01) |
| *C07D 253/00* | (2006.01) |
| *C07D 237/26* | (2006.01) |
| *C07D 237/28* | (2006.01) |
| *C07D 239/00* | (2006.01) |

(52) U.S. Cl. ............ 544/179; 544/180; 544/235; 544/242; 544/350; 546/113

(58) Field of Classification Search .......... 546/113; 544/179, 180, 235, 242, 350
See application file for complete search history.

(56) References Cited

U.S. PATENT DOCUMENTS

2001/0014754 A1  8/2001  Suzuki et al.
2005/0176706 A1*  8/2005  Bekkali et al. ........... 514/234.5

FOREIGN PATENT DOCUMENTS

WO   WO03082280   10/2003
WO   WO2005090343   9/2005

OTHER PUBLICATIONS

Hong, et al: "Synthesis and protein kinase C inhibitory activities of indane analogs of balanol" 1996, p. 973-978, vol. 6, No. 8, Bioorganic and Medicinal Chemistry Letters, Sphinks Pharmaceuticals, NC, USA.
International Search Report, PCT/US2006/036157, Jan. 16, 2007.

* cited by examiner

*Primary Examiner*—D. Magaret Seaman
*Assistant Examiner*—Niloofar Rahmani
(74) *Attorney, Agent, or Firm*—Michael P. Morris; Mary-Ellen M. Devlin; Timothy X. Witkowski

(57) ABSTRACT

A process for stereoselective synthesis of a compound of Formula (I)

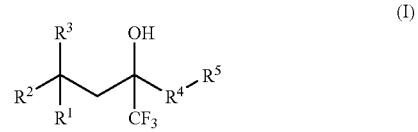

wherein $R^1$, $R^2$, $R^3$, $R^4$, and $R^5$ are as described herein.

31 Claims, No Drawings

STEREOSELECTIVE SYNTHESIS OF CERTAIN TRIFLUOROMETHYL-SUBSTITUTED ALCOHOLS

RELATED APPLICATIONS

This application claims benefit of U.S. Ser. No. 60/722,145, filed Sep. 30, 2005, which is hereby incorporated by reference in its entirety.

FIELD OF THE INVENTION

The present invention relates to an efficient stereoselective synthesis of certain trifluoromethyl-substituted alcohols.

BACKGROUND OF THE INVENTION

Trifluoromethyl-substituted alcohols of Formula (I) have been described as ligands that bind to the glucocorticoid receptor.

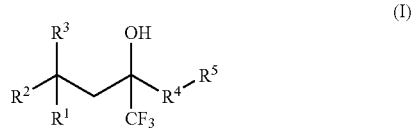

(I)

These compounds are effective as therapeutics in treating a number of diseases modulated by glucocorticoid receptor function, including inflammatory, autoimmune and allergic disorders. Examples of these compounds are described in U.S. Patent Application Publication Nos. 2003/0232823 and 2004/0029932, and U.S. Pat. No. 6,903,215, which are each incorporated herein by reference in their entireties and are hereinafter termed "the Trifluoromethyl-Substituted Alcohol Patent Applications".

It is well known in the art that enantiomers of a particular compound can have different biological properties including efficacy, toxicity, and pharmacokinetic properties. Thus, it is often desirable to administer one enantiomer of a racemic therapeutic compound.

The synthetic methods disclosed in the patent applications cited above describe the synthesis of racemic products. Separation of enantiomers was accomplished by chiral HPLC and may be accomplished by other conventional ways of separating enantiomers. Chiral HPLC and other enantiomer separation method, however, are generally unsuitable for large-scale preparation of a single enantiomer. Thus, a stereoselective synthesis for preparation of these compounds would be highly desirable.

The present invention discloses an efficient stereoselective synthesis of certain compounds of Formula (I). A key step involves an efficient chiral resolution of a beta-hydroxy acid and a one-step synthesis of a 6-azaindole subunit. The novel one-step azaindole synthesis from an ester has been previously described in our U.S. Ser. No. 11/070,462, which is incorporated by reference. This new synthesis has fewer steps and utilizes relatively inexpensive starting materials, therefore providing a more economical synthesis of the drug substance.

SUMMARY OF THE INVENTION

The instant invention is directed to a process for stereoselective synthesis of a compound of Formula (I)

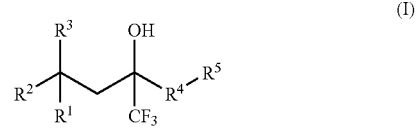

(I)

wherein:
$R^1$ is an aryl or heteroaryl group, each optionally substituted with one to three substituent groups,
wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, $C_1$-$C_5$ alkanoyloxy, $C_1$-$C_5$ alkanoyl, aroyl, trifluoromethyl, trifluoromethoxy, or $C_1$-$C_5$ alkylthio,
wherein each substituent group of $R^1$ is optionally independently substituted with one to three substituent groups selected from methyl, methoxy, fluoro, chloro, or alkoxy;
$R^2$ and $R^3$ are each independently hydrogen or $C_1$-$C_5$ alkyl, or $R^2$ and $R^3$ together with the carbon atom they are commonly attached to form a $C_3$-$C_8$ spiro cycloalkyl ring;
$R^4$ is $C_1$-$C_5$ alkyl, $C_2$-$C_5$ alkenyl, or $C_2$-$C_5$ alkynyl, each optionally substituted with one to three substituent groups,
wherein each substituent group of $R^4$ is independently $C_1$-$C_3$ alkyl, hydroxy, halogen, amino, or oxo; and
$R^5$ is the moiety

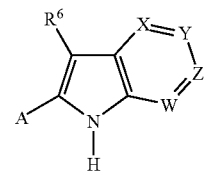

wherein A is the point of attachment to $R^4$,
W, X, Y, or Z is N or CH and at least one of W, X, Y, or Z is N, and $R^6$ is H, alkyl, or aryl, and
$R^5$ is optionally substituted with one to three substituent groups, wherein each substituent group of $R^5$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, trifluoromethylthio, nitro, or amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
wherein each substituent group of $R^5$ is optionally independently substituted with one to three substituent groups selected from $C_1$-$C_3$ alkyl, $C_1$-$C_3$ alkoxy, halogen, hydroxy, oxo, cyano, amino, or trifluoromethyl, the process comprising:

(a) reacting a starting material of formula A with an unsaturated ester of formula B in the presence of a suitable acid, without a solvent or with a suitable solvent, at a suitable temperature to provide an ester of formula C

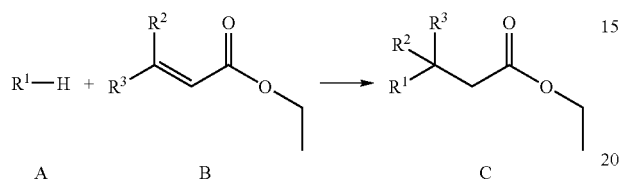

(b) hydrolyzing the ester of formula C using a suitable base in water, with or without an organic solvent, at a suitable temperature to provide an acid of formula D

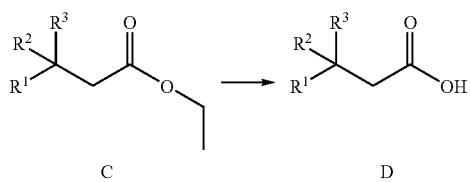

(c) reacting the acid of formula D with TFAA, in the presence of a suitable base in a suitable solvent at a suitable temperature to provide a trifluoromethyl ketone of formula E

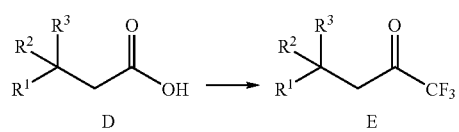

(d) reacting the trifluoromethyl ketone of formula E with an acetate in the presence of a suitable base in a suitable solvent at a suitable temperature to prepare an ester of formula F

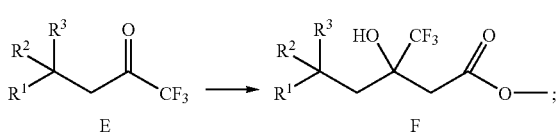

(e) hydrolyzing the ester of formula F with a suitable base in a suitable solvent at a suitable temperature to obtain an acid of formula G

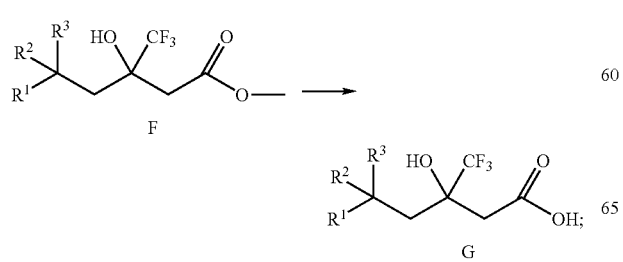

(f) reacting the acid of formula G with a suitable resolving base to provide a pure diastereomer followed by reacting the pure diastereomer with a suitable base in a suitable solvent at a suitable temperature to provide a pure enantiomer of formula H, or reacting a pure diastereomer of the acid of formula G with a suitable acid in a suitable solvent at a suitable temperature to obtain a pure enantiomer of formula H

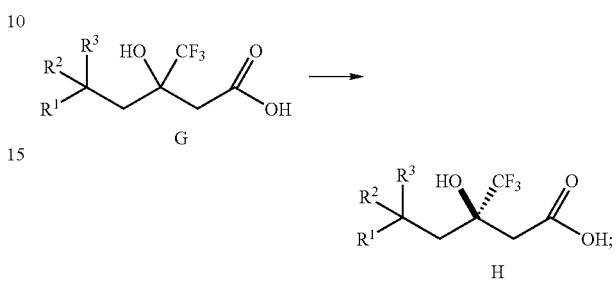

(g) reacting the acid of formula H followed with a suitable alcohol, R'—OH, where R' is an alkyl group, followed by protection of the tertiary alcohol with a protecting group agent PG-Y, where Y is a leaving group, at a suitable temperature to obtain the ester of formula I

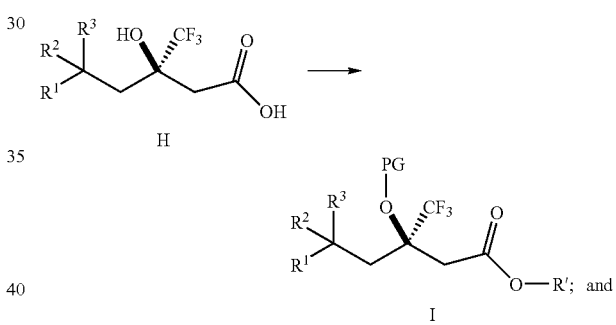

(h) reacting the ester of formula I with a compound of formula J, wherein W, X, Y, or Z is N or CH, at least one of W, X, Y, or Z is N, and $R^6$ is H, alkyl, or aryl, in the presence of a suitable base in a suitable solvent at a suitable temperature to obtain a compound of Formula (1)

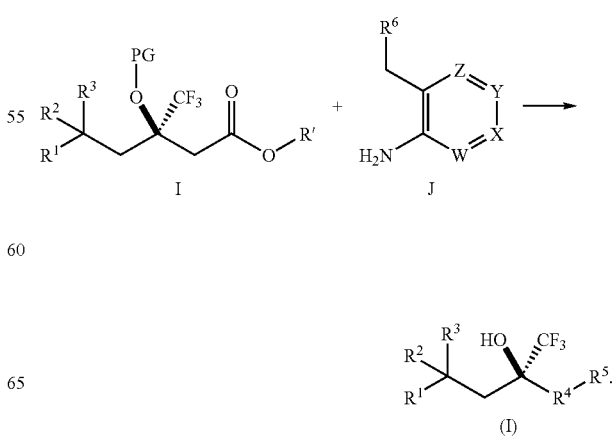

In an aspect of the invention, the suitable solvent of step (a) is no solvent, carbon tetrachloride, carbon disulfide, hydrocarbons such as heptane, hexane, chlorobenzene, or a mixture thereof, preferably no solvent. In another aspect of the invention, the suitable acid of step (a) is protonic acids such as HCl, sulfuric acid, phosphoric acid, alkyl or aryl sulfonic acids or Lewis acids such as $TiCl_4$, $AlCl_3$, preferably methane sulfonic acid. In another aspect of the invention, the suitable temperature of step (a) is 0° C. to 180° C.

In an aspect of the invention, the suitable solvent of step (b) is water, alkyl alcohols such as MeOH, EtOH, or dimethyl ether, diethyl ether, dipropyl ether, diisopropyl ether, dibutyl ether, tetrahydrofuran (THF), ethylene glycol dimethyl ether (DME), tert-butyl methyl ether (MTBE), or a mixture thereof, preferably MeOH and water. In another aspect of the invention, the suitable base of step (b) is metal hydroxides such as NaOH or KOH. In another aspect of the invention, the suitable temperature of step (b) is 0° C. to 100° C.

In an aspect of the invention, the suitable solvent of step (c) is hydrocarbons such as toluene, xylene, heptane or alkyl ethers such as dimethyl ether, diethyl ether, dipropyl ether, diisopropyl ether, dibutyl ether, tetrahydrofuran (THF), ethylene glycol dimethyl ether (DME), tert-butyl methyl ether (MTBE), or a mixture thereof, preferably toluene or xylene. In another aspect of the invention, the suitable base of step (c) is pyridine, lutidine, or amine bases such as triethylamine or Hünig base, preferably pyridine. In another aspect of the invention, the suitable temperature of step (c) is 20° C. to 150° C.

In an aspect of the invention, the suitable solvent of step (d) is THF, DME, diethyl ether, dipropyl ether, diisopropyl ether, dibutyl ether, MTBE, toluene, xylene, or dimethylformamide (DMF). In another aspect of the invention, the suitable base of step (d) is lithium hexamethyldisilazide (LiHMDS), sodium hexamethyldisilazide (NaHMDS), potassium hexamethyldisilazide (KHMDS), LDA, LiH, NaH, KH, or $NaNH_2$. In another aspect of the invention, the suitable acetate reagent of step (d) is methyl acetate, ethyl acetate, propyl acetate, or butyl acetate. In another aspect of the invention, the suitable temperature of step (d) is −70° C. to 50° C.

In another aspect of the invention, the suitable solvent of step (e) is methanol, ethanol, propanol, isopropyl alcohol, butanol, tert-butanol, diethyl ether, dipropyl ether, diisopropyl ether, dibutyl ether, tetrahydrofuran (THF), ethylene glycol dimethyl ether (DME), tert-butyl methyl ether (MTBE), or a mixture thereof, preferably tetrahydrofuran. In another aspect of the invention, the suitable base of step (e) is potassium hydroxide, sodium hydroxide, or lithium hydroxide. In another aspect of the invention, the suitable temperature of step (e) is −40° C. to 80° C.

In yet another aspect of the invention, the suitable resolving base of step (f) is (+ or −) cis-1-amino-2-indanol, quinine, quinidine, (+ or −) ephedrine, (+ or −) deoxyephedrine, (+ or −) methylbenzylamine, (+ or −) (1-naphthyl)ethylamine, or (+ or −) (2-naphthyl)ethylamine. In another aspect of the invention, the suitable base of step (f) is potassium hydroxide, lithium hydroxide, sodium bicarbonate, sodium carbonate, potassium bicarbonate, potassium carbonate, or lithium carbonate. Alternatively, a pure enantiomer of formula H is obtained by reacting a pure diastereomer with a suitable acid, such as hydrochloric acid, sulfuric acid. In another aspect of the invention, the suitable solvent of step (f) is dichloromethane, diethyl ether, ethyl acetate, or MTBE. In another aspect of the invention, the suitable temperature of step (f) is −10° C. to 150° C.

In another aspect of the invention, the esterification of step (g) is carried out by treatment of the free acid with methanol in the presence of an acid catalyst selected from sulfuric acid, hydrochloric acid, acetic acid, p-toluenesulfonic acid, and acetic acid. In another aspect of the invention, in the protecting group agent PG-Y of step (g), the protecting group PG is a trialkylsilyl group, lower alkyl ether (e.g., methoxymethyl ether (MOM ether)), lower alkyl group, or internally protected as a β-lactone with the terminal carboxyl group, and the leaving group Y is Cl, Br, I, MsO, TsO, and TfO, preferably TfO. In another aspect of the invention, the suitable solvent of step (g) is dichloromethane. In another aspect of the invention, the suitable temperature of step (g) is 0° C. to 150° C.

In another aspect of the invention, the suitable solvent of step (h) is THF, DME, diethyl ether, dipropyl ether, diisopropyl ether, dibutyl ether, MTBE, toluene, benzene, xylene, hexane, pentane, heptane, methylene chloride, or a mixture thereof, and is preferably THF. In another aspect of the invention, the suitable base of step (h) is n-BuLi, sec-BuLi, tert-BuLi, or LDA, optionally including additives such as N,N,N',N'-tetramethylethylenediamine (TMEDA), β-dialkylaminoalcohols, sparteine, or polyethers, preferably sec-BuLi. In another aspect of the invention, the suitable temperature of step (h) is −70° C. to 50° C.

In another aspect of the invention, the compound of formula J is 3-amino-4-picoline, 4-amino-3-picoline, 2-amino-3-picoline, or 3-amino-2-picoline, each optionally substituted on the ring or methyl group with a substituent compatible with alkyl lithium, preferably 3-amino-4-picoline.

While certain specific embodiments of the invention, including specific reaction conditions, solvents, protecting groups, and other reagents and reactants are described above in detailing various aspects of the invention, it should be understood that no particular limitation to these specific embodiments or aspects should limit the invention in its broadest sense. Accordingly, the invention should be understood to include none, some, or all of these various aspects in various combinations.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1$-$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar—, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, decenyl, and the like.

The terms "alkynyl" or "alkynyl group" mean a branched or straight-chain aliphatic hydrocarbon monovalent radical containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkenylene" or "alkenylene group" mean a branched or straight-chain aliphatic hydrocarbon divalent radical having the specified number of carbon atoms and at least one carbon-carbon double bond. This term is exemplified by groups such as ethenylene, propenylene, n-butenylene, and the like, and may alternatively and equivalently be denoted herein as -(alkylenyl)-.

The terms "alkynylene" or "alkynylene group" mean a branched or straight-chain aliphatic hydrocarbon divalent radical containing at least one carbon-carbon triple bond. This term is exemplified by groups such as ethynylene, propynylene, n-butynylene, 2-butynylene, 3-methylbutynylene, n-pentynylene, heptynylene, octynylene, decynylene, and the like, and may alternatively and equivalently be denoted herein as -(alkynyl)-.

The terms "alkoxy" or "alkoxy group" mean a monovalent radical of the formula AlkO—, where Alk is an alkyl group. This term is exemplified by groups such as methoxy, ethoxy, propoxy, isopropoxy, butoxy, sec-butoxy, tert-butoxy, pentoxy, and the like.

The terms "aryloxy", "aryloxy group", mean a monovalent radical of the formula ArO—, where Ar is aryl. This term is exemplified by groups such as phenoxy, naphthoxy, and the like.

The terms "alkylcarbonyl", "alkylcarbonyl group", "alkanoyl", or "alkanoyl group" mean a monovalent radical of the formula AlkC(O)—, where Alk is alkyl or hydrogen.

The terms "arylcarbonyl", "arylcarbonyl group", "aroyl" or "aroyl group" mean a monovalent radical of the formula ArC(O)—, where Ar is aryl.

The terms "acyl" or "acyl group" mean a monovalent radical of the formula RC(O)—, where R is a substituent selected from hydrogen or an organic substituent. Exemplary substituents include alkyl, aryl, arylalkyl, cycloalkyl, heterocyclyl, heteroaryl, heteroarylalkyl, and the like. As such, the terms comprise alkylcarbonyl groups and arylcarbonyl groups.

The terms "acylamino" or "acylamino group" mean a monovalent radical of the formula RC(O)N(R)—, where each R is a substituent selected from hydrogen or a substituent group.

The terms "alkoxycarbonyl" or "alkoxycarbonyl group" mean a monovalent radical of the formula AlkO—C(O)—, where Alk is alkyl. Exemplary alkoxycarbonyl groups include methoxycarbonyl, ethoxycarbonyl, tert-butyloxycarbonyl, and the like.

The terms "alkylaminocarbonyloxy" or "alkylaminocarbonyloxy group" mean a monovalent radical of the formula R$_2$NC(O)O—, where each R is independently hydrogen or lower alkyl.

The term "alkoxycarbonylamino" or "alkoxycarbonylamino group" mean a monovalent radical of the formula ROC(O)NH—, where R is lower alkyl.

The terms "alkylcarbonylamino" or "alkylcarbonylamino group" or "alkanoylamino" or "alkanoylamino groups" mean a monovalent radical of the formula AlkC(O)NH—, where Alk is alkyl. Exemplary alkylcarbonylamino groups include acetamido (CH$_3$C(O)NH—).

The terms "alkylaminocarbonyloxy" or "alkylaminocarbonyloxy group" mean a monovalent radical of the formula AlkNHC(O)O—, where Alk is alkyl.

The terms "amino" or "amino group" mean an —NH$_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —NR$_2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "alkoxycarbonylamino" or "alkoxycarbonylamino group" mean a monovalent radical of the formula AlkOC(O)NH—, where Alk is alkyl.

The terms "ureido" or "ureido group" mean a monovalent radical of the formula R$_2$NC(O)NH—, where each R is independently hydrogen or alkyl.

The terms "halogen" or "halogen group" mean a fluoro, chloro, bromo, or iodo group.

The term "halo" means one or more hydrogen atoms of the group are replaced by halogen groups.

The terms "alkylthio" or "alkylthio group" mean a monovalent radical of the formula AlkS—, where Alk is alkyl. Exemplary groups include methylthio, ethylthio, n-propylthio, isopropylthio, n-butylthio, and the like.

The terms "sulfonyl" or "sulfonyl group" mean a divalent radical of the formula —SO$_2$—.

The terms "carbocycle" or "carbocyclic group" mean a stable aliphatic 3- to 15-membered monocyclic or polycyclic monovalent or divalent radical consisting solely of carbon and hydrogen atoms which may comprise one or more fused or bridged ring(s), preferably a 5- to 7-membered monocyclic or 7- to 10-membered bicyclic ring. Unless otherwise specified, the carbocycle may be attached at any carbon atom which results in a stable structure and, if substituted, may be substituted at any suitable carbon atom which results in a stable structure. The term comprises cycloalkyl (including spiro cycloalkyl), cycloalkylene, cycloalkenyl, cycloalkenylene, cycloalkynyl, and cycloalkynylene, and the like.

The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornanyl, adamantyl, tetrahydronaphthyl (tetralin), 1-decalinyl, bicyclo[2.2.2]octanyl, 1-methylcyclopropyl, 2-methylcyclopentyl, 2-methylcyclooctyl, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, and the like.

The term "compounds of the invention" and equivalent expressions are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The term "leaving group" means a group with the meaning conventionally associated with it in synthetic organic chemistry, that is, an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

The term "solvent" or "suitable solvent" means a solvent or a mixture of solvents that is substantially inert under the conditions of the reaction being described in conjunction therewith, including, for example, dimethyl ether, diethyl ether, dipropyl ether, diisopropyl ether, dibutyl ether, tetrahydrofuran (THF), ethylene glycol dimethyl ether (DME), tert-butyl methyl ether (MTBE), benzene, toluene, acetonitrile, N,N-dimethylformamide, chloroform, methylene chloride, dichloroethane, ethyl acetate, acetone, methyl ethyl ketone, methanol, ethanol, propanol, isopropanol, tert-butanol, dioxane, pyridine, and the like, or mixtures thereof. Unless specified to the contrary, the solvents used in the reactions of the present invention are substantially inert solvents.

The term "protecting group" means a chemical group which selectively blocks one reactive site in a multifunctional compound such that a chemical reaction can be carried out selectively at another unprotected reactive site in the meaning conventionally associated with it in synthetic chemistry. Certain synthetic steps of the invention rely upon the protective groups to block reactive atoms, for example, nitrogen or hydrogen atoms, present in the reactants. For example, an amino protecting group or nitrogen protecting group is an organic group intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Similarly, a hydroxy protecting group is an organic group intended to protect the oxygen atom of a hydroxyl group against undesirable reactions during synthetic procedures. Exemplary hydroxy protecting groups include, but are not limited to benzyl, silyl groups, tetrahydropyranyl, esters, and the like. One of skill in the art, based on the instant specification, will know how to chose a suitable protecting group for the ease of removal and for the ability to withstand the subsequent reactions. Certain protecting groups are described, for example, in J. F. W. McOmie (ed.), *Protective Groups in Organic Chemistry*, Plenum Press, 1973; T. W. Greene & P. G. M. Wuts, *Protective Groups in Organic Synthesis* (3rd Ed.), John Wiley & Sons, 1999; and P. J. Kocienski, *Protecting Groups* ($2^{nd}$ Ed.) Theime Medical Pub., 2000, each of which is incorporated by reference in its entirety. Protecting groups may be removed at a convenient subsequent stage using methods known in the art or by metabolic or other in vivo administration conditions.

The term "protecting group agent" means reaction conditions or a reagent that supplies a desired protecting group to the substrate.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 $R^5$, then such group is optionally substituted with up to two $R^5$ groups and $R^5$ at each occurrence is selected independently from the defined list of possible $R^5$. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

EXPERIMENTAL EXAMPLES

The invention provides processes for making compounds of Formula (I). In all schemes, unless specified otherwise, $R^1$ to $R^5$ in the formulas below can have the meanings of $R^1$ to $R^5$ set forth herein and additionally in the Trifluoromethyl-Substituted Alcohol Patent Applications. Intermediates used in the preparation of compounds of the invention are either commercially available or readily prepared by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Experimental Examples section. Typically, reaction progress may be monitored by high performance liquid chromatography (HPLC) or thin layer chromatography (TLC), if desired, and intermediates and products may be purified by chromatography on silica gel and/or by recrystallization.

Synthetic Example

The following is a representative example that illustrates the process of the invention. HPLC used to characterize products and intermediates were done on a $C_{18}$ Super-ODS column (Supelco, part No. 818197, 4.6 mm×10 cm) eluting with a gradient of 5% acetonitrile/95% water/0.05% TFA to 95% acetonitrile/5% water/0.05% TFA over 15 minutes and then held at 95% acetonitrile/5% water/0.05% TFA for 5 minutes. References to concentration or evaporation of solutions refer to concentration on a rotary evaporator.

Example 1

Synthesis of (R)-1,1,1-Trifluoro-4-(5-bromo-2-methoxyphenyl)-4-methyl-2-(1H-pyrrolo[2,3-c]pyridin-2-ylmethyl)pentan-2-ol

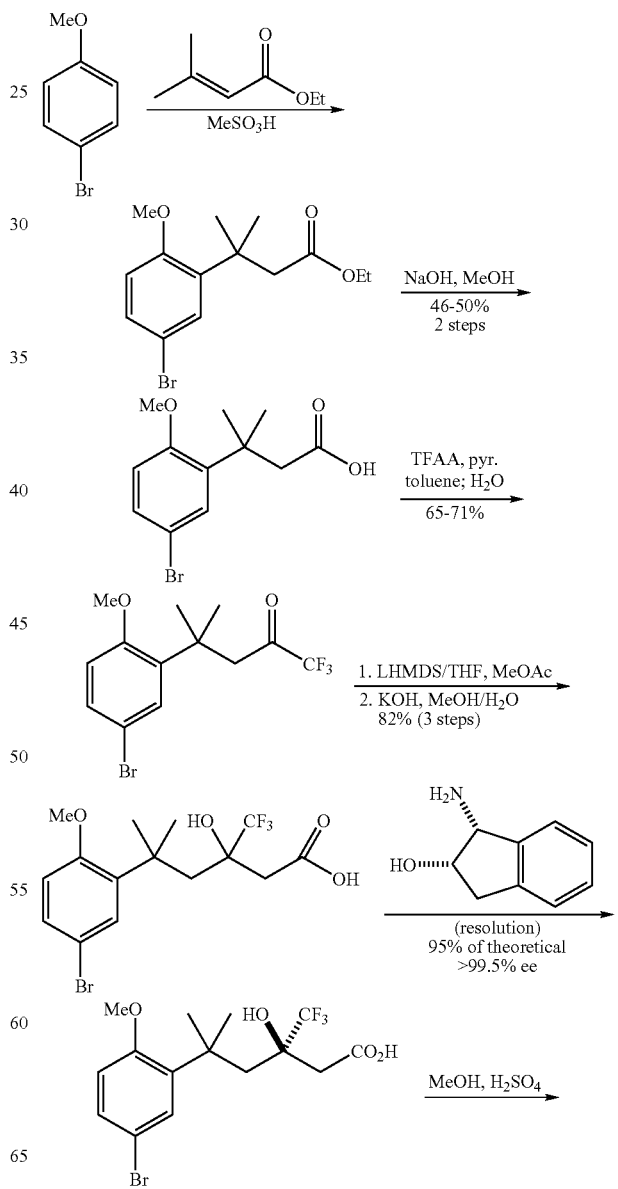

-continued

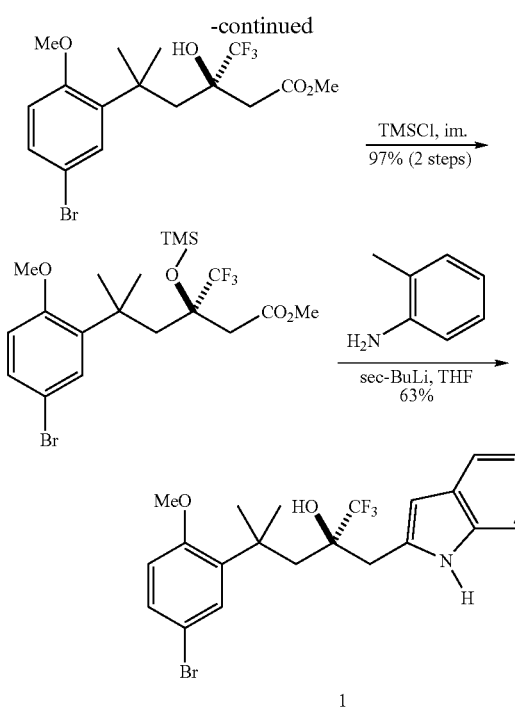

The details of the synthesis are as follows.

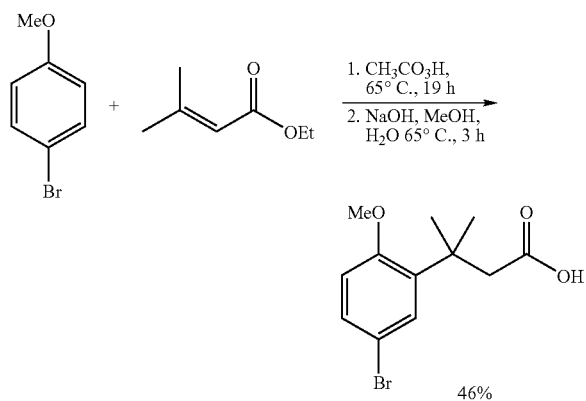

287 g (2.24 mole) of ethyl 3,3-dimethylacrylate and 420 mL (3.36 mole) of 4-bromoanisole were charged into a three-neck 5 L flask under nitrogen. To this 944 mL of methanesulfonic acid was added in one portion with stirring. $T_{int}$ rose from 18.6° C. to 25.6° C. The reaction mixture was heated at $T_{int}$=65° C. for 19 hours. HPLC indicated ~60% conversion of ethyl 3,3-dimethylacrylate to product. The reaction mixture was cooled with the aid of an ice water bath to $T_{int}$=15.0° C. 1 L of water was then added by addition funnel at a rate to keep $T_{int}$ below 40° C. After addition, the temperature was brought to ~20° C. and 1 L of heptane was added and the mixture was stirred vigorously for 5 minutes. The layers were separated. HPLC of aqueous layer showed no product. The organic layer was washed with two 500 mL portions of water and concentrated in vacuo to give 879 g of crude product which was dissolved in 1 L of methanol. A solution of 358.4 g of NaOH in 1 L of water was then added. The reaction mixture was heated at $T_{int}$=65° C. for 3 hours. HPLC showed complete conversion of the ester to the corresponding acid. The reaction mixture was cooled with an ice water bath to $T_{int}$=18.0° C. 1 L of water was added and the reaction mixture was extracted with 1 L of $CH_2Cl_2$. The aqueous layer was acidified to pH of 1 with concentrated HCl while cooling with ice water bath. The aqueous layer was extracted with two 1 L portions of EtOAc and the organic extracts were concentrated in vacuo to give the crude product. 800 mL of hexane was added to the crude product and the mixture was stirred vigorously for 30 minutes. The mixture was filtered and the solid was washed with hexanes to give the pure product. After drying under high vacuum, 294.2 g of white granular solid was obtained (46% yield). HPLC: 99.8 area %.

Additional product remained in the filtrate.

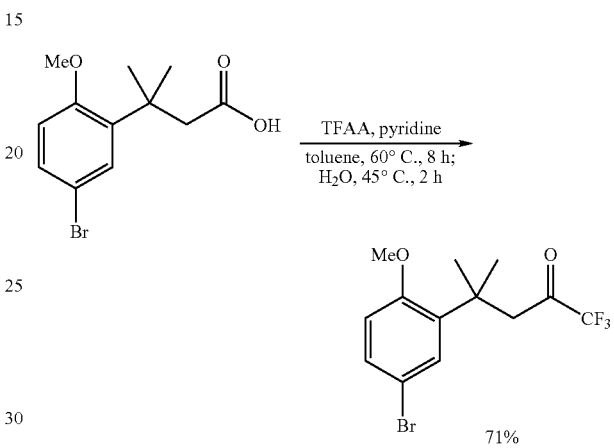

800 g (2.79 mole) of the starting carboxylic acid was charged in a 22 L flask. 4 L of toluene was then added and the resultant slurry was stirred at $T_{int}$=21.0° C. under $N_2$ flow while 2.36 L (16.7 mole) of TFAA was added in one portion. $T_{int}$=15.0° C. after addition and homogenous solution was obtained. The reaction mixture was cooled to $T_{int}$=9.0° C. with a dry ice/IPA bath ($T_{ext}$=−30° C.) and 1.81 L (22.3 mole) of pyridine was added by addition funnel. $T_{int}$=16.7° C. after addition. The dry ice/IPA bath was replaced with a heating mantle and the reaction mixture was heated to $T_{int}$=60° C. over 45 minutes. A moderate reflux was observed. The reaction color turned gradually from light yellow to dark brown. After 8 hours at $T_{int}$=60° C. the heating was stopped and the reaction mixture was allowed to cool to $T_{int}$=27.9° C. over 14.5 hours. The reaction mixture was cooled to $T_{int}$=9.0° C. with dry ice/IPA bath ($T_{ext}$=−50° C.). 2 L of water was added dropwise by addition funnel (caution: exothermic!). Dry ice was added as needed during the addition to maintain internal temperature between 9.0° C.-37.0° C. After the first ~400 mL (20%) of water was added, the exotherm was much less vigorous. The addition required ~30 minutes. After addition, the cooling bath was removed and replaced with a heating mantle. The reaction mixture was heated at $T_{int}$=45° C. for 2 hours. HPLC showed conversion of all intermediates to product. After cooling to room temperature, 200 g of NaCl was added and the reaction mixture was stirred vigorously for 5 minutes. The layers were separated and the organic layer washed with 2 L of water followed by 2 L of 2 N aqueous NaOH solution and finally with 2 L of water to give ~4.1 L of a dark brown solution. This was concentrated in vacuo and washed with two 300 mL portions of toluene and dried under high vacuum to give 742.8 g of crude product as a dark brown oil. HPLC assay showed 91.0 wt % product (676.0 g, 71%). KF=0.01% (105.2 ppm), HPLC 91.7 area %.

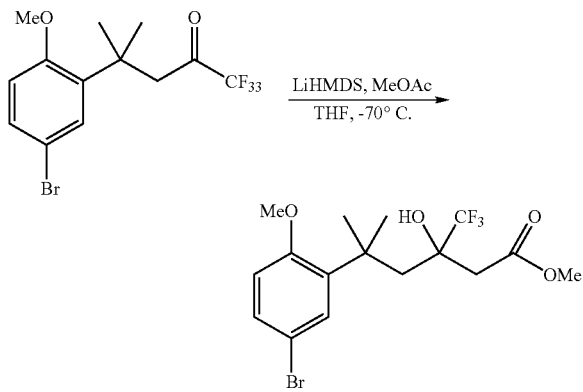

77.3 mL (0.973 mole) of methyl acetate was charged into a 5 L flask under $N_2$. 1.1 L of THF was charged via cannula and the reaction mixture was cooled to $T_{int}=-70°$ C. 778 mL (0.778 mole) of LiHMDS (1 M in THF) was added via cannula over 20 minutes. The reaction mixture was allowed to stir at $T_{int}=-70°$ C. for 30 minutes. A solution of 165 g (0.487 mole) of the trifluoromethyl ketone in 300 mL of THF was added dropwise over 20 min ($T_{int}$ maintained at less than $-67°$ C. during addition). The reaction mixture was stirred for 15 minutes. HPLC indicated the reaction was complete. It was then quenched with 900 mL of saturated aqueous $NH_4Cl$ solution and extracted with 2×600 mL of $CH_2Cl_2$. The organic extracts were concentrated in vacuo to give 256.2 g of crude product which was used in the next step HPLC: 96.6 area %.

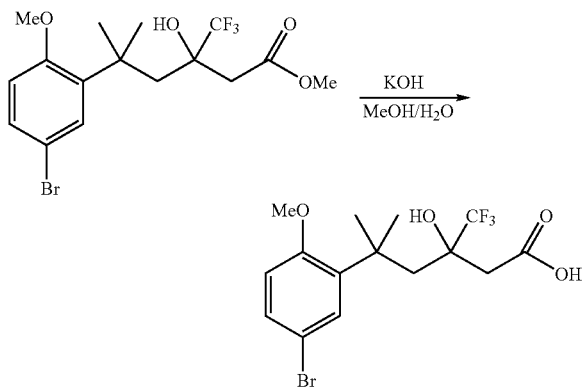

256.2 g (0.487 mole) of the above crude methyl ester was dissolved in 1.0 L of MeOH, in a 5 L flask. A solution of 136.5 g (2.43 mole) of KOH in 1.0 L of water was added. A yellow precipitate formed immediately. The reaction mixture was stirred at ambient temperature for 16 hours. HPLC showed complete conversion to product. 1.0 L of water was added and the reaction mixture was extracted with 1.0 L of $CH_2Cl_2$. The aqueous layer was acidified to pH=1 with 10% aqueous HCl solution and was extracted with 2×1.0 L of $CH_2Cl_2$. The organic layer was dried ($MgSO_4$), filtered and concentrated in vacuo to give 179.8 g of the desired acid as a tan solid (93% over 2 steps) HPLC: 100 area %.

4.04 g of the crude acid (10.12 mmoles) was dissolved in 13.7183 g (15.0 mL) of EtOAc and the solution was heated to 75° C. 0.682 g (4.5714 mmoles, 0.4517 equiv) of (+)-cis-1-amino-2-indanol was added to the solution and the solution was seeded with 15 mg of the desired diastereomer. After 10 minutes, the semi-solid suspension was further diluted with 2.6152 g (3.0 mL) of EtOAc at 78° C. and aged for 10 minutes. The resulting slurry was treated with 4 portions, over 40 minutes at 10 minute intervals, of 0.171 g (0.1133 equivalents) of the (+)-cis-1-amino-2-indanol until a total of 1.3660 g (9.1562 millimoles, 9.048 equivalents) had been added. After stirring for 1 h the batch was cooled to 20° C. over 1.5 hours using a linear ramp (38.7° C./h) and then aged at 20° C. for 1 hour. The slurry was filtered and washed with 15 mL of EtOAc in 3.5 mL portions and dried for 1 hour on the filter funnel using vacuum. Obtained 2.6 g (93% based on the desired enantiomer) of the resolved product. TGA loss<1%, ee 99.61%.

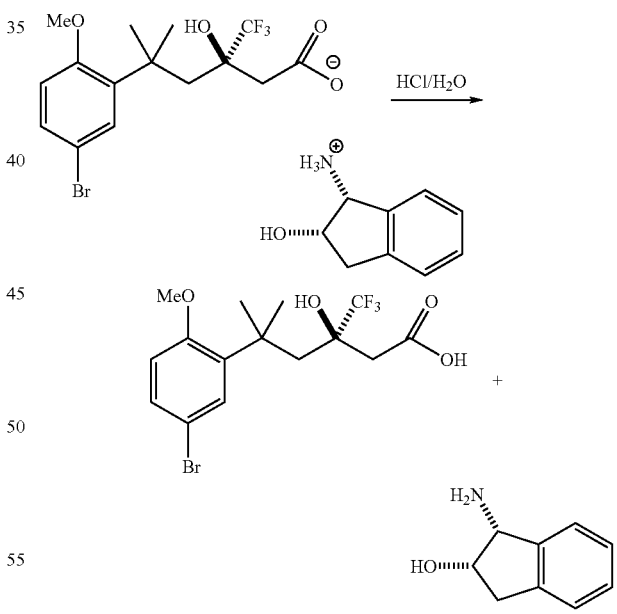

773.3 g (1.410 mole) of salt was suspended in 2.0 L of EtOAc. The suspension was stirred while 2.0 L of 2 N aqueous HCl solution was added. The mixture was stirred until the salt dissolved (~20 minutes). The layers were separated and the aqueous layer was extracted with 0.5 L of EtOAc. The combined organic layers were filtered through a short (1 cm) pad of $SiO_2$ and concentrated in vacuo to give ~660 g of a viscous oil. This was washed with 1 L of MeOH and dried on high-vacuum for ~80 hours to give 592.5 g of a white crystalline solid. HPLC: 99.5 area %. $^1$H NMR showed the pure acid and a small amount of MeOH. The aqueous layer may be made basic and extracted to recover the aminoindanol.

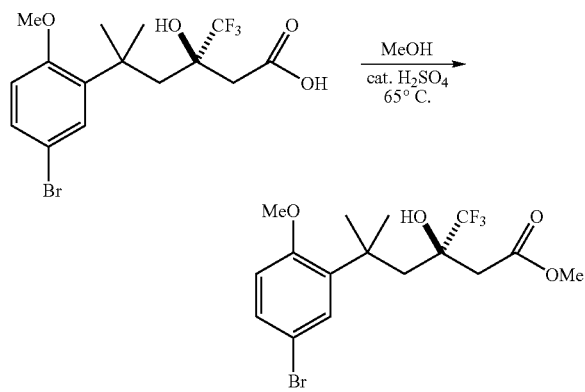

91.85 g (0.230 mole) of the above acid was dissolved in 0.82 L of MeOH. 16 mL of concentrated $H_2SO_4$ was then added and the reaction mixture was heated at $T_{int}=65°$ C. for 14 hours. HPLC showed 99.3 area % product. After cooling to ambient temperature, the reaction mixture was concentrated in vacuo to ~½ volume and 0.8 L of EtOAc was added followed by careful addition of 2×500 mL of saturated aqueous $NaHCO_3$ solution. The organic layer was dried ($MgSO_4$), filtered and concentrated in vacuo to give 95.8 g of the pure product as a white crystalline solid. HPLC: 100 area %.

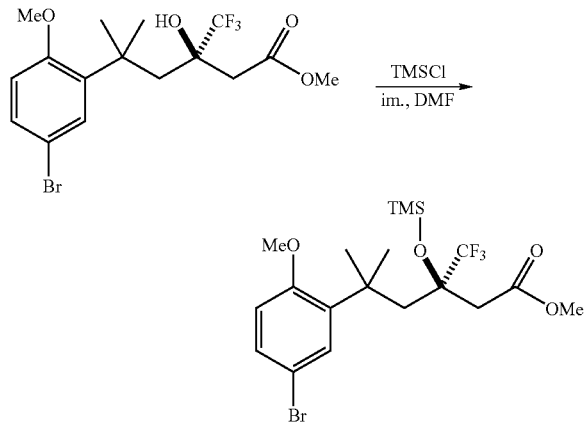

39.1 g (0.574 mole) of imidazole was charged in a 3 L flask. A solution of 95.8 g (0.230 mole) of starting material in 0.46 L of DMF was added and the mixture was stirred until a clear solution was obtained. 43.7 mL (0.335 mole) of TMSCl was added dropwise over 20 minutes by addition funnel and the reaction mixture was stirred at ambient temperature for 46 hours. HPLC: 98.5 area % product. 0.8 L of hexanes and 0.8 L of water were then added and the mixture was stirred vigorously for 10 minutes. The layers were separated and the aqueous layer was extracted with 0.4 L of hexanes. The combined organic extracts were washed with 0.8 L of water and 0.8 L of saturated $NaHCO_3$ solution and were dried over magnesium sulfate, filtered through a short (½") pad of $SiO_2$, and concentrated in vacuo to give 108.1 g of the desired product as a colorless oil, 97% over 2 steps. HPLC: 100 area %.

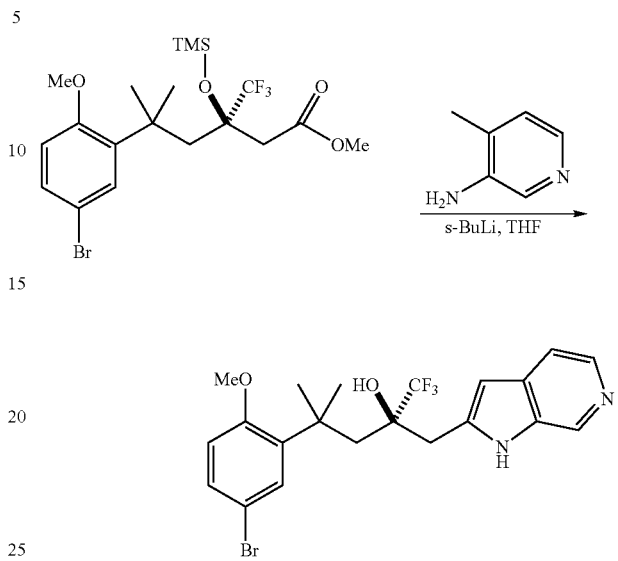

59.5 g (0.550 mol) of 3-amino-4-methylpyridine was charged into a dry flask under $N_2$. 2.36 L of anhydrous THF was added via cannula and the mixture was stirred and cooled to $T_{int}=-65°$ C. 786 mL (1.10 mol) of sec-BuLi (1.4 M/cyclohexane) was added via cannula at a rate to keep $T_{int}$ below $-50°$ C. (~50 minutes). The reaction mixture was allowed to warm to $T_{int}=15°$ C. over 3 hours, 20 minutes. An orange slurry was obtained. The reaction mixture was cooled to $T_{int}=-45°$ C. and 80.5 g (0.166 mol) of the methyl ester in 85 mL of anhydrous THF was added dropwise over ~5 minutes. The reaction mixture was stirred for 30 min ($T_{int}$ rises to $-35°$ C.). HPLC showed no starting ester. The reaction was cooled to $T_{int}=-60°$ C. and quenched with 315 mL of 6 N HCl while $T_{int}$ was kept below $-30°$ C. (5 minutes). The reaction was stirred until it reached room temperature. The reaction mixture was allowed to stand at room temperature, overnight. The layers were separated. The organic layer was washed with 310 mL of saturated $NaHCO_3$ solution and concentrated in vacuo to an orange oil. This oil was dissolved in 2.4 L of methanol and the solution was cooled to $T_{int}=12°$ C. A solution of 200 mL of 2 N NaOH was added over 1 minutes. The ice bath was removed and the reaction mixture was stirred at room temperature for 1.5 hours. HPLC showed the deprotection was complete. 80 mL of 6 N HCl solution was added to bring the pH to ~7. The solvent was evaporated in vacuo to give an orange oil. 2.4 L of MTBE and 1 L of water were added. After mixing, the layers were separated and the organic layer was washed with 0.5 L of saturated $NaHCO_3$ solution and then with 0.5 L of brine. The organic layer was concentrated in vacuo to give 82.4 g of a tan solid. 250 mL of MTBE was added to give a clear solution. After stirring a white solid precipitate formed. The mixture was stirred at room temperature for 19 hours, filtered, and the solid washed with the filtrate followed by 1:1 MTBE/hexane, air dried and finally dried under high vacuum to give 58.4 g (63%) of the title compound as a white powdery solid. HPLC showed 96.7 area %. $^1$H NMR shows an MTBE solvate.

We claim:
1. A process for stereoselective synthesis of a compound of Formula (I)

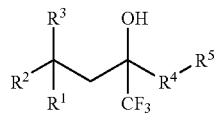

wherein:
R$^1$ is an aryl or heteroaryl group, each optionally substituted with one to three substituent groups,
  wherein each substituent group of R$^1$ is independently C$_1$-C$_5$ alkyl, C$_2$-C$_5$ alkenyl, C$_2$-C$_5$ alkynyl, C$_3$-C$_8$ cycloalkyl, heterocyclyl, aryl, heteroaryl, C$_1$-C$_5$ alkoxy, C$_2$-C$_5$ alkenyloxy, C$_2$-C$_5$ alkynyloxy, aryloxy, C$_1$-C$_5$ alkanoyloxy, C$_1$-C$_5$ alkanoyl, aroyl, trifluoromethyl, trifluoromethoxy, or C$_1$-C$_5$ alkylthio,
    wherein each substituent group of R$^1$ is optionally independently substituted with one to three substituent groups selected from methyl, methoxy, fluoro, chloro, or alkoxy;
R$^2$ and R$^3$ are each independently hydrogen or C$_1$-C$_5$ alkyl, or R$^2$ and R$^3$ together with the carbon atom they are commonly attached to form a C$_3$-C$_8$ spiro cycloalkyl ring;
R$^4$ is C$_1$-C$_5$ alkyl, C$_2$-C$_5$ alkenyl, or C$_2$-C$_5$ alkynyl, each optionally substituted with one to three substituent groups,
  wherein each substituent group of R$^4$ is independently C$_1$-C$_3$ alkyl, hydroxy, halogen, amino, or oxo; and
R$^5$ is the moiety

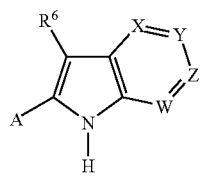

wherein A is the point of attachment to R$^4$,
W, X, Y, or Z is N or CH and at least one of W, X, Y, or Z is N, and
R$^6$ is H, alkyl, or aryl, and
R$^5$ is optionally substituted with one to three substituent groups, wherein each substituent group of R$^5$ is independently C$_1$-C$_5$ alkyl, C$_2$-C$_5$ alkenyl, C$_2$-C$_5$ alkynyl, C$_3$-C$_8$ cycloalkyl, heterocyclyl, aryl, heteroaryl, C$_1$-C$_5$ alkoxy, C$_2$-C$_5$ alkenyloxy, C$_2$-C$_5$ alkynyloxy, aryloxy, acyl, C$_1$-C$_5$ alkoxycarbonyl, C$_1$-C$_5$ alkanoyloxy, aminocarbonyl, alkylaminocarbonyl, dialkylaminocarbonyl, aminocarbonyloxy, C$_1$-C$_5$ alkylaminocarbonyloxy, C$_1$-C$_5$ dialkylaminocarbonyloxy, C$_1$-C$_5$ alkanoylamino, C$_1$-C$_5$ alkoxycarbonylamino, C$_1$-C$_5$ alkylsulfonylamino, aminosulfonyl, C$_1$-C$_5$ alkylaminosulfonyl, C$_1$-C$_5$ dialkylaminosulfonyl, halogen, hydroxy, carboxy, cyano, trifluoromethyl, trifluoromethoxy, trifluoromethylthio, nitro, or amino wherein the nitrogen atom is optionally independently mono- or di-substituted by C$_1$-C$_5$ alkyl; or ureido wherein either nitrogen atom is optionally independently substituted with C$_1$-C$_5$ alkyl; or C$_1$-C$_5$ alkylthio wherein the sulfur atom is optionally oxidized to a sulfoxide or sulfone,
  wherein each substituent group of R$^5$ is optionally independently substituted with one to three substituent groups selected from C$_1$-C$_3$ alkyl, C$_1$-C$_3$ alkoxy, halogen, hydroxy, oxo, cyano, amino, or trifluoromethyl,
the process comprising:
(a) reacting a starting material of formula A with an unsaturated ester of formula B in the presence of a suitable acid, without a solvent or with a suitable solvent, at a suitable temperature to provide an ester of formula C

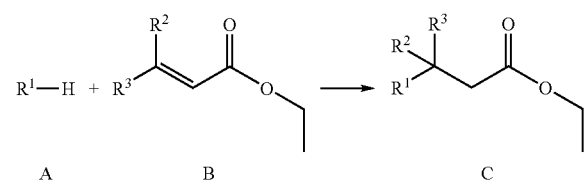

(b) hydrolyzing the ester of formula C using a suitable base in water, with or without an organic solvent, at a suitable temperature to provide an acid of formula D

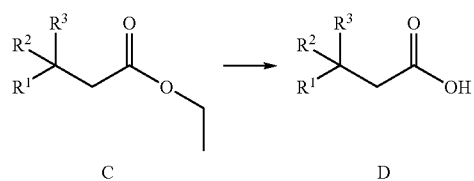

(c) reacting the acid of formula D with TFAA, in the presence of a suitable base in a suitable solvent at a suitable temperature to provide a trifluoromethyl ketone of formula E

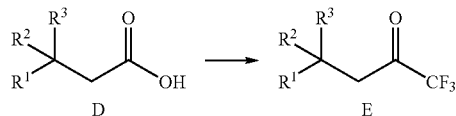

(d) reacting the trifluoromethyl ketone of formula E with an acetate in the presence of a suitable base in a suitable solvent at a suitable temperature to prepare an ester of formula F

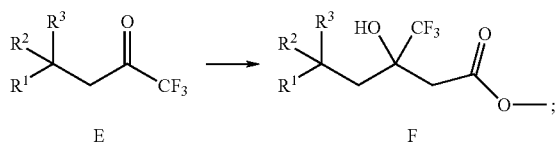

(e) hydrolyzing the ester of formula F with a suitable base in a suitable solvent at a suitable temperature to obtain an acid of formula G

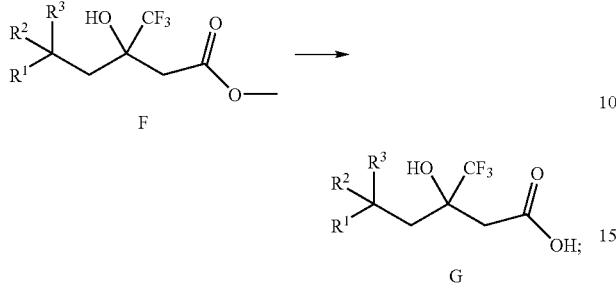

(f) reacting the acid of formula G with a suitable resolving base to provide a pure diastereomer followed by reacting the pure diastereomer with a suitable base in a suitable solvent at a suitable temperature to provide a pure enantiomer of formula H, or reacting a pure diastereomer of the acid of formula G with a suitable acid in a suitable solvent at a suitable temperature to obtain a pure enantiomer of formula H

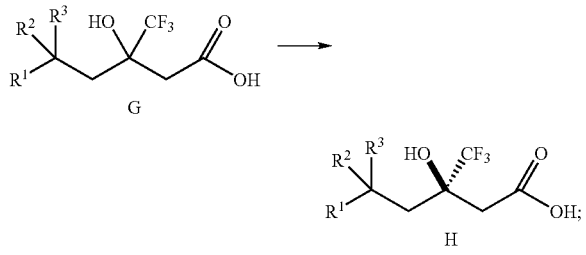

(g) reacting the acid of formula H followed with a suitable alcohol, R'—OH, where R' is an alkyl group, followed by protection of the tertiary alcohol with a protecting group agent PG-Y, where Y is a leaving group, at a suitable temperature to obtain the ester of formula I

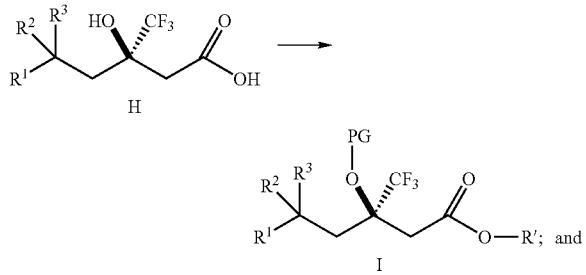

(h) reacting the ester of formula I with a compound of formula J, wherein W, X, Y, or Z is N or CH, at least one of W, X, Y, or Z is N, and $R^6$ is H, alkyl, or aryl, in the presence of a suitable base in a suitable solvent at a suitable temperature to obtain a compound of Formula (I)

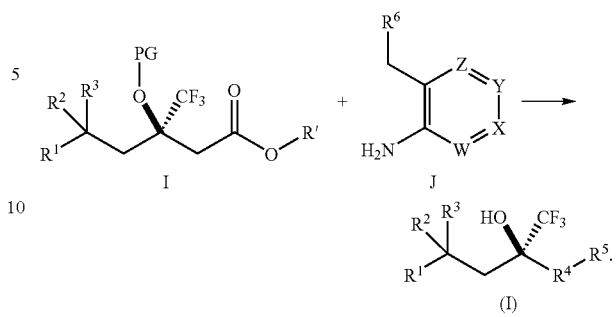

2. The process according to claim 1, wherein the suitable solvent of step (a) is carbon tetrachloride, carbon disulfide hydrocarbons such as heptane, hexane or a mixture thereof.

3. The process according to claim 1, wherein no solvent is used of step (a).

4. The process according to claim 1, wherein the suitable acid of step (a) is hydrochloric acid, sulfuric acid, phosphoric acid, an alkyl or aryl sulfonic acid, or $TiCl_4$, or $AlCl_3$.

5. The process according to claim 1, wherein the suitable temperature of step (a) is 0° C. to 180° C.

6. The process according to claim 1, wherein the suitable solvent of step (b) is water, an alkyl alcohol, dimethyl ether, diethyl ether, dipropyl ether, diisopropyl ether, dibutyl ether, tetrahydrofuran, ethylene glycol dimethyl ether, tert-butyl methyl ether, or a mixture thereof.

7. The process according to claim 1, wherein the suitable base of step (b) is a metal hydroxide.

8. The process according to claim 1, wherein the suitable temperature of step (b) is 0° C. to 100° C.

9. The process according to claim 1, wherein the suitable solvent of step (c) is toluene, xylene, heptane, dimethyl ether, diethyl ether, dipropyl ether, diisopropyl ether, dibutyl ether, tetrahydrofuran, ethylene glycol dimethyl ether, tert-butyl methyl ether, or a mixture thereof.

10. The process according to claim 1, wherein the suitable base of step (c) is pyridine, lutidine, triethylamine, or Hünig base.

11. The process according to claim 1, wherein the suitable temperature of step (c) is 20° C. to 150° C.

12. The process according to claim 1, wherein the suitable solvent of step (d) is tetrahydrofuran, ethylene glycol dimethyl ether, tert-butyl methyl ether, diethyl ether, dipropyl ether, diisopropyl ether, dibutyl ether toluene, xylene, or dimethylformamide.

13. The process according to claim 1, wherein the suitable base of step (d) is lithium hexamethyldisilazide (LiHMDS), sodium hexamethyldisilazide (NaHMDS), potassium hexamethyldisilazide (KHMDS), LDA, LiH, NaH, KH, or $NaNH_2$.

14. The process according to claim 1, wherein the suitable acetate reagent of step (d) is methyl acetate, ethyl acetate, propyl acetate, or butyl acetate.

15. The process according to claim 1, wherein the suitable temperature of step (d) is −70° C. to 50° C.

16. The process according to claim 1, wherein the suitable solvent of step (e) is methanol, ethanol, propanol, isopropyl alcohol, butanol, tert-butanol, diethyl ether, dipropyl ether, diisopropyl ether, dibutyl ether, tetrahydrofuran, ethylene glycol dimethyl ether, tert-butyl methyl ether, or a mixture thereof.

17. The process according to claim 1, wherein the suitable base of step (e) is potassium hydroxide, sodium hydroxide, or lithium hydroxide.

18. The process according to claim 1, wherein the suitable temperature of step (e) is −40° C. to 80° C.

19. The process according to claim 1, wherein the suitable resolving base of step (f) is (+ or −) cis-1-amino-2-indanol, quinine, quinidine, (+ or −) ephedrine, (+ or −) deoxyephedrine, (+ or −) methylbenzylamine, (+ or −) (1-naphthyl)ethylamine, or (+ or −)(2-naphthyl)ethylamine.

20. The process according to claim 1, wherein the suitable base of step (f) is potassium hydroxide, lithium hydroxide, sodium bicarbonate, sodium carbonate, potassium bicarbonate, potassium carbonate, or lithium carbonate.

21. The process according to claim 1, wherein the suitable acid of step (f) is hydrochloric acid, sulfuric acid, hydrobromic acid, hydroiodic acid, phosphoric acid, methanesulfonic acid, p-tolyl sulfonic acid, or other aryl or alkyl sulfonic acid.

22. The process according to claim 1, wherein the suitable solvent of step (f) is dichloromethane, diethyl ether, ethyl acetate, or tert-butyl methyl ether.

23. The process according to claim 1, wherein the suitable temperature of step (f) is −10° C. to 150° C.

24. The process according to claim 1, wherein the esterification of step (g) is carried out by treatment of the free acid with methanol in the presence of an acid catalyst selected from sulfuric acid, hydrochloric acid, acetic acid, p-toluenesulfonic acid, and acetic acid.

25. The process according to claim 1, wherein in the protecting group agent PG-Y of step (g), the protecting group PG is a trialkylsilyl group, lower alkyl ether, lower alkyl group, or internally protected as a β-lactone with the terminal carboxyl group, and the leaving group Y is Cl, Br, I, MsO, TsO, and TfO.

26. The process according to claim 1, wherein the suitable solvent of step (g) is dichloromethane.

27. The process according to claim 1, wherein the suitable temperature of step (g) is 0° C. to 150° C.

28. The process according to claim 1, wherein the suitable solvent of step (h) is tetrahydrofuran, ethylene glycol dimethyl ether, tert-butyl methyl ether, diethyl ether, dipropyl ether, diisopropyl ether, dibutyl ether, toluene, benzene, xylene, hexane, pentane, heptane, methylene chloride, or a mixture thereof.

29. The process according to claim 1, wherein the suitable base of step (h) is n-BuLi, sec-BuLi, or tert-BuLi, optionally including additives such as N,N,N',N'-tetramethylethylenediamine (TMEDA), β-dialkylaminoalcohols, sparteine, or polyethers.

30. The process according to claim 1, wherein the suitable temperature of step (h) is −70° C. to 50° C.

31. The process according to claim 1, wherein the compound of formula J is 3-amino-4-picoline, 4-amino-3-picoline, 2-amino-3-picoline, or 3-amino-2-picoline, each optionally substituted on the ring or methyl group with a substituent compatible with alkyl lithium.

* * * * *